(12) United States Patent
Pan

(10) Patent No.: US 8,193,240 B2
(45) Date of Patent: Jun. 5, 2012

(54) COMPOSITIONS AND METHODS FOR REDUCING OR PREVENTING OBESITY

(75) Inventor: Yuanlong Pan, Chesterfield, MO (US)

(73) Assignee: Nestec S.A., Vevey (CH)

( * ) Notice: Subject to any disclaimer, the term of this patent is extended or adjusted under 35 U.S.C. 154(b) by 491 days.

(21) Appl. No.: 11/082,557

(22) Filed: Mar. 17, 2005

(65) Prior Publication Data

US 2005/0222050 A1 Oct. 6, 2005

Related U.S. Application Data

(60) Provisional application No. 60/553,871, filed on Mar. 17, 2004.

(51) Int. Cl.
*A61K 31/13* (2006.01)
*A61K 31/14* (2006.01)
*A61K 31/20* (2006.01)
*A61K 31/35* (2006.01)
(52) U.S. Cl. ......... 514/453; 514/558; 514/579; 514/642
(58) Field of Classification Search .................. 514/453, 514/558, 579, 642
See application file for complete search history.

(56) References Cited

U.S. PATENT DOCUMENTS

| | | | | |
|---|---|---|---|---|
| 5,554,646 | A * | 9/1996 | Cook et al. ..................... | 514/560 |
| 6,204,291 | B1 * | 3/2001 | Sunvold et al. ................ | 514/556 |
| 6,335,038 | B1 | 1/2002 | Cavazza ......................... | 424/757 |
| 6,359,017 | B1 * | 3/2002 | Bruckner et al. ............. | 424/757 |
| RE38,155 | E | 6/2003 | Brown et al. .................... | 426/2 |
| 2001/0000786 | A1 | 5/2001 | Sunvold et al. ............... | 514/556 |
| 2001/0041187 | A1 * | 11/2001 | Hastings et al. .............. | 424/439 |
| 2002/0010141 | A1 | 1/2002 | Ingram ............................ | 514/27 |
| 2002/0111466 | A1 | 8/2002 | Hendler et al. .................... | 536/8 |
| 2004/0248822 | A1 | 12/2004 | Bruckner et al. ............... | 514/27 |
| 2006/0147607 | A1 * | 7/2006 | Beaver et al. .................. | 426/622 |

FOREIGN PATENT DOCUMENTS

| | | |
|---|---|---|
| EP | 0 628 258 A1 | 12/1994 |
| EP | 1 300 404 A1 | 4/2003 |
| EP | 0 848 955 B1 | 7/2003 |
| GB | 2 355 382 A | 4/2001 |
| JP | 2002/80351 | 3/2002 |
| WO | 97/35491 A1 | 10/1997 |
| WO | 01/17374 A1 | 3/2001 |
| WO | 03/013268 A1 | 2/2003 |
| WO | 03/068218 A1 | 8/2003 |
| WO | 2004/014155 A2 | 2/2004 |
| WO | 2004/071211 A1 | 8/2004 |
| WO | 2004/084885 A1 | 10/2004 |
| WO | 2005/058064 A1 | 6/2005 |

OTHER PUBLICATIONS

STN online, file BIOSIS, Acc. No. 2007:329822, (Pan, FASEB Journal (2007), vol. 21, No. 5, pp. A373), Abstract.*
STN online, file SCISEARCH, Acc. No. 2001:434992 (Rahman et al., Nutrition (2001), vol. 17, No. 5, pp. 385-390), Abstract.*
STN online, file BIOSIS, Acc. No. 2001:54667, (Watson et al., Journal of Veterinary Internal Medicine (2000), vol. 14, No. 6, pp. 598-608), Abstract.*
Naaz et al., The Soy Isoflavone Genistein Decreases Adipose Deposition in Mice, Endocrinology (2003), vol. 144, No. 8, pp. 3315-3320.*
Merriam-Webster's Collegiate Dictionary, 10th edition, Merriam-Webster, Inc.,: Springfield, Massachusets, 1996, p. 41.*
Bhathena S.J., et al., "Beneficial role of dietary phytoestrogens in obesity and diabetes," *Am. J. Clin. Nutr.*, 2002, 76, 1191-1201.
Cerundolo, R., et al., "Identification and concentration of soy phytoestrogens in commercial dog foods," *Am. J. Vet res.*, 2004, 65(5), 592-596.
Chin, S.F., et al., "Dietary sources of conjugated dienoic isomers of linoleic acid, a newly recognized class of anticarcinogens," *J. Food Comp. Anal.*, 1992, 5, 185-197.
Clarkson, T.B., et al., "Inhibition of postmenopausal atherosclerosis progression: a comparison of the effects of conjugated equine estrogens and soy phytoestrogens," *J Clin Endocrinol Metab.*, 2001, 86(1), 41-47.
Cooke, P.S., et al., "Role of estrogens in adipocyte development and function," *Exp. Biol Med*, 2004, 229, 1127-1135.
Court, M.H., et al., "Identification and concentration of soy isoflavones in commercial cat foods," *Am. J. Vet Res.*, 2002, 63(2), 181-185.
Davi, G., et al., "Lipid peroxidation in diabetes mellitus," *Antioxid Redox Signal*, 2005, 7, 256-268.
Derwent Publications, "Preparation astaxanthin contain powdery composition by drying and pulverize crustacean at 0-35 deg. C, useful as feed additive," JP1186346, 1988, XP-002342472, 1 page (Abstract).
Fang, Y.C., et al., "Effect of genistein supplementation on tissue genistein and lipid peroxidation of serum, liver and low-density lipoprotein in hamsters," *J. Nutr. Biochem.*, 2004, 15, 142-148.
Harper, E.J., et al.,."Effects of feeding regimens on bodyweight, composition and condition score in cats following ovariohysterectomy," *J Small Anim Pract*, 2001, 42, 433-438 (Abstract only).
Jiang, F., et al., "Cardiovascular protective effects of synthetic isoflavone derivatives in apolipoprotein E-deficient mice," *J. Vas Res.*, 2003, 40, 276-284.
Kandulska, K., et al., "Effect of some phytoestrogens on metabolism of rat adipocytes," *Reprod Nutr Dev*, 1999, 39, 497-501.
Kang, J.O., et al., "Effect of astaxanthin on the hepatotoxicity, lipid peroxidation and antioxidative enzymes in the liver of CC14-treated rats," *Dept. of Pharmacology, School of Dentistry, Kyung Hee University*, S. Korea, 2001, 23(2), 79-84, 1 page (Abstract).

(Continued)

*Primary Examiner* — James H. Alstrum-Acevedo
(74) *Attorney, Agent, or Firm* — Potter Anderson & Corroon LLP

(57) ABSTRACT

Compositions useful for weight management in an animal are disclosed. The compositions comprise one or more isoflavones or isoflavone metabolites, and in some embodiments include conjugated linoleic acid, and/or L-carnitine. Also disclosed are methods useful for weight management in an animal utilizing compositions comprising one or more isoflavones, conjugated linoleic acid, and/or L-carnitine. Preferably, the compositions and methods employ a combination of one or more isoflavones, or a combination of one or more isoflavones in conjunction with conjugated linoleic acid, and L-carnitine.

14 Claims, 12 Drawing Sheets

OTHER PUBLICATIONS

Kawakami, Y., et al., "Regulative actions of dietary soy isoflavone on biological antioxidative system and lipid metabolism in rats," *J. Agric. Food. Chem.*, 2004, 52, 1764-1768.

Linford, N.J., et al., "17β-estradiol and the phytoestrogen genistein attenuate neuronal apoptosis induced by the endoplasmic reticulum calcium-ATPase inhibitor thapsigargin," *Steroids*, 2002, 67, 1029-1040.

Lynch, S.M., et al., "Formation of non-cyclooxygenasae-derived prostanoids ($F_2$-isoprostanes) in plasma and low density lipoprotein exposed to oxposed to oxidative stress in vitro," *J. Clin. Invest.*, 1994, 93, 998-1004.

Mohamed, M.K., et al., "Effect of long-term ovariectomy and estrogen replacement on the expression of estrogen receptor gene in female rats," *Eur. J. Endocrinol.*, 2000, 142, 307-314.

Montuschi, P., et al., "Isoprostanes: markers and mediators of oxidative stress," *FASEB J.*, 2004, 18, 1791-1800.

Morrow, J.D., et al., "A series of prostaglandin $F_2$-like compounds are produced in vivo in humans by a non-cyclooxygenase, free radical-catalyzed mechanism," *Proc. Natl. Acad. Sci.*, 1990, 87, 9383-9387.

Naaz, A., et al., "The soy isoflavone genistein decreases adipose deposition in mice," *Endocrinol.*, 2003, 144, 3315-3320.

Pergola G.D., "The adipose tissue metabolism: role of testosterone and dehydroepiandrosterone," *Int. J. Obesity*, 2000, 24, S59-S63.

Robertson, I.D., "The association of exercise, diet and other factors with owner-perceived obesity in privately owned dogs from metropolitan perth," *WA. Prev. Vet Med.*, 2003, 58, 75-83.

Sayegh, R.A., et al., "Impact of hormone replacement therapy on the body mass and fat compositions of menopausal women: a cross-sectional study," *Menopause*, 1999, 6, 312-315 (Abstract only).

Setchell, K.D.R., et al., "The clinical importance of the metabolite equol-a clue to the effectiveness of soy and its isoflavones," *J. Nutr.*, 2002, 132, 3577-3584.

Stocker, R., et al., "Role of oxidative modifications in atherosclerosis," *Physiol Rev*, 2004, 84, 1381-1478.

Tzu-Hua, W., et al., Annual Meeting of Professional Research Scientists on Experimental Biology, New Orleans, LA, Apr. 20-24, 2002, ISSN 0892-6638, Meeting Abstract, XP-002342435, 1 page.

Urakawa, H., et al., "Oxidative stress is associated with adiposity and insulin resistance in men," *J Clin Endocrinol Metab*, 2003, 88(10), 4673-4676.

Wagner, J.D., et al., "Soy protein with isoflavones, but not an isoflavone-rich supplement, improves arterial low-density lipoprotein metabolism and atherogenesis," *Arterioscler Thromb Vasc Biol.*, 2003, 23, 2241-2246.

* cited by examiner

COMPOSITIONS AND METHODS FOR REDUCING OR PREVENTING OBESITY

This claims benefit of U.S. Provisional Application No. 60/553,871, filed Mar. 17, 2004, the entire contents of which are incorporated by reference herein.

FIELD OF THE INVENTION

The invention relates to nutrition of companion and other domestic animals. In particular, the invention provides compositions and methods in which isoflavones, conjugated linoleic acid, and L-carnitine are used alone or in combination in food, food supplements and the like, for weight management in animals.

BACKGROUND OF THE INVENTION

Similar to humans, companion animals such as dogs and cats can become obese. The result of excessive accumulation of adipose tissue (body fat) results in animals being overweight or obese.

Adipose tissue is an important energy depot. This is important for the survival of wild animals because their daily food supply is limited and uncertain. However, the body fat level in wild animals is much lower than that of domesticated animals.

It has been estimated that 25-44% of domesticated dogs and cats are overweight or obese in the United States and Europe (Hand, M S, Armstrong P J, Allen T A. Obesity: Occurrence, treatment, and prevention. Vet Clin North Am Small Anim Pract. 1989, 19:447-474; Scarlett J M, Donoghue S, Saidla J, Wills J. Overweight cats: prevalence and risk factors. Int. J. Obes. 1994, 18:S22-S28). Dogs that are overweight or obese have health problems, especially in middle age (i.e., dogs that are between 6-8 years old). If these health problems caused by being overweight are not corrected, the risks increase for the development of a number of chronic diseases, including diabetes mellitus, cancer, hypertension, pulmonary, cardiovascular, and degenerative joint disease. In addition, a dog may suffer from skin problems, reduced resistance to infectious diseases, and increased mortality. Increased oxidative stress is, at least partially, believed to be responsible for the increased risk of the above-mentioned diseases associated with obesity. Further, it is well known that obesity places stress on an animal's body.

In addition to its role as an energy surplus storage site, adipose tissue is an endocrine organ. The endocrine system controls a variety of functions in an animal's body through hormones and cytokines. The homeostasis of these hormones is disturbed in obesity.

Leptin is a protein hormone that functions to regulate appetite, metabolism and sexual maturation. Leptin is synthesized in fat cells (adipocytes) and secreted into the blood stream. Therefore, serum levels of leptin correlate with the amount of body fat. Leptin concentrations increase during overfeeding or weight gain and decrease during fasting or weight loss. It has been shown in humans that leptin highly correlates to how much fat is stored in a body, with greater levels found in individuals with more fat and reduced levels in those who dieted. Similarly, it has been shown that in obese dogs, the plasma concentration of leptin was increased regardless of the dogs' breed, age or sex.

It is known that leptin's effects on body weight are mediated through its effects on hypothalamic centers that control body temperature, energy expenditure, as well food intake. It has been shown that other hormones or endocrine substances involved in body weight regulation or its distribution, such as catecholamines, corticosteroids, insulin, sex hormones, and growth hormone, can be triggered by leptin.

Certain pro-inflammatory cytokines are synthesized in adipose tissue. For example, Tumor Necrosis Factor-$\alpha$ (TNF-$\alpha$) is synthesized in adipocytes and acts locally. In normal animals, TNF-$\alpha$ regulates the number of adipocytes, reduces fat accumulation and promotes fat breakdown. TNF-$\alpha$ also stimulates leptin synthesis and secretion from adipocytes. TNF-$\alpha$ inhibits insulin action; increased TNF-$\alpha$ leads to insulin resistance.

Interleukin-6 (IL-6) is another pro-inflammatory cytokine associated with adipose tissue. In normal animals, IL-6 reduces fat accumulation, suppresses appetite and increases fat breakdown. IL-6 stimulates the secretion of acute-phase proteins (e.g., C-reactive protein) by the liver. Synthesis and secretion of IL-6 by adipocytes may be one of the major sources of circulating IL-6. Circulating IL-6 concentrations are strongly correlated with adiposity.

Excess adipose tissue results in a hyperactive endocrine adipose organ, which, in turn, affects other endocrine systems (e.g., insulin etc), metabolic functions, oxidative stress level, and inflammation.

Increased oxidative stress has been linked with obesity. Isoprostanes are a stable in vivo marker of oxidative stress and tissue damage (Lynch S M, Morrow J D, Roberts II L J, Frei B. Formation of non-cyclooxygenasae-derived prostanoids ($F_2$-isoprostanes) in plasma and low density lipoprotein exposed to oxidative stress in vitro. J. Clin. Invest. 1994, 93: 998-1004; Morrow J D, Hill K E, Burk R F, Nammour T M, Badr K F, Roberts II L J, A series of prostaglandin $F_2$-like compounds are produced in vivo in humans by a non-cyclooxygenase, free radical-catalyzed mechanism, Proc. Natl. Acad. Sci. 1990, 87: 9383-9387). Isoprostanes are produced in vivo by oxidative damage of arachidonic acid in cell membrane phospholipids and lipoproteins in the blood. They are a chemically stable end-product of lipid peroxidation. Isoprostanes released by phospholipases from membrane phospholipids and lipoprotein particles circulate in the plasma and are excreted in urine. Higher levels of isoprostanes in the blood and urine mean higher oxidative stress and tissue damage in vivo.

Obese men have been found to have significantly higher plasma concentrations of isoprostanes than nonobese men ($P<0.05$). The plasma levels of isoprostanes were significantly correlated with body mass index ($r=0.408$; $P<0.05$), body fat weight ($r=0.467$; $P<0.05$), visceral ($r=0.387$; $P<0.05$) and total fat area ($r=0.359$; $P<0.05$) in all (obese and nonobese) men. (Urakawa H, Katsuki A, Sumida Y, Gabazza E C, Murashima S, Morioka K, Maruyama N, Kitagawa N, Tanaka T, Hori Y, Nakatani K, Yano Y, Adachi Y, Oxidative stress is associated with adiposity and insulin resistance in men. J Clin Endocrinol Metab, October 2003; 88(10):4673-6).

Obesity per se can lead directly to hypertension. This has been shown in dogs in which obesity was induced by feeding them a high-fat diet. It has been shown that weight gain in the dog is associated with an increase in blood pressure, heart rate, cardiac output, and glomerular filtration rate. In addition, these dogs showed a progressive alternation in cardiac diastolic function. Angiotensinogen is released into the blood where it serves as a precursor for two proteins: angiotensin I and angiotensin II. The actions of these proteins lead to an increase in blood pressure through the reabsorption of sodium in the kidney.

Animals accumulate fat by eating more calories than are expended as energy. If the intake of energy exceeds its expenditure, fat accumulates. If fat is to be removed from the body, fewer calories must be consumed or more calories must be used than consumed. Physical activity changes the expenditure of energy. For example, a marked decrease in physical activity may lead to obesity. Physical inactivity restricts energy expenditure and may contribute to increased food intake. The basal metabolic rate (BMR) is the energy expended by an animal in a resting state and represents the energy required to perform normal body functions.

Excessive accumulation of body fat in animals results in excessive weight gain and obesity. This occurs when fat synthesis exceeds fat breakdown. Substances that inhibit fat synthesis and/or promote fat breakdown may be used to either reduce or prevent excessive weight gain or obesity in animals. Current weight loss diets result in loss of both body fat and lean body mass. In addition, current weight loss diets are not designed to reduce the oxidative damage caused by obesity.

An additional risk factor for obesity in animals is removal of the sex organs. Procedures such as neutering, spaying, ovariectomy, castration, and the like, are frequently performed on animals for population control. However, weight gain is commonly observed in animals following these procedures. (Harper E J, Stack D M, Watson T D, Moxham G. Effects of feeding regimens on bodyweight, composition and condition score in cats following ovariohysterectomy. J Small Anim Pract. 2001, 42:433-438; Robertson I D. The association of exercise, diet and other factors with owner-perceived obesity in privately owned dogs from metropolitan Perth, W A. Prev Vet Med. 2003, 58:75-83.) It is believed that the weight gain is a consequence of the diminished production of sex hormones by the sex organs and markedly decreased levels of endogenous sex hormones following the removal of the sex organs.

Among the sex hormones, estrogens and androgens have been found to play a role in the metabolism of adipose tissue. Indeed, diminished levels of estrogen and testosterone have been correlated with increased accumulation of body fat. (Pergola G D, The adipose tissue metabolism: Role of testosterone and dehydroepiandrosterone. Int. J. Obesity, 2000, 24: S59-S63; Cooke P S and Naaz A. Role of Estrogens in Adipocyte Development and Function. Exp Biol Med. 2004, 229:1127-1135; Mohamed, M K et al., Effect of long-term ovariectomy and estrogen replacement on the expression of estrogen receptor gene in female rats. Eur. J. Endocrinol. 2000, 142:307-314.) The sex hormones may affect adipose tissue in different ways, for example, by affecting the number and size of adipocytes, lipogenesis, and lipolysis, modulating appetite or energy expenditure, and the like. (Pergola G D, The adipose tissue metabolism: Role of testosterone and dehydroepiandrosterone. Int. J. Obesity, 2000, 24: S59-S63; Cooke P S and Naaz A. Role of Estrogens in Adipocyte Development and Function. Exp Biol Med. 2004, 229:1127-1135; Naaz, A et al. The soy isoflavone genistein decreases adipose deposition in mice. Endocrinol. 2003, 144:3315-3320). In this regard, hormone replacement therapy and dietary supplementation have been studied as a means to reverse these effects. (Sayegh, R A et al. Impact of hormone replacement therapy on the body mass and fat compositions of menopausal women: a cross-sectional study. Menopause. 1999, 6:312-315; Blathena S J et al. Beneficial role of dietary phytoestrogens in obesity and diabetes. Am. J. Clin. Nutr. 2002, 76:1191-1201).

With respect to dietary supplementation, mounting evidence suggests that phytoestrogens may play a role in enhancing lipid metabolism and diminishing deposition of adipose tissue. (Naaz, A et al. 2003; Bhathena, S J et al. 2002; and Wagner J D, et al. Soy protein with isoflavones, but not an isoflavone-rich supplement, improves arterial low-density lipoprotein metabolism and atherogenesis. Arterioscler Thromb Vasc Biol. 2003, 23:2241-2246).

Phytoestrogens are chemicals produced by plants that have a similar structure to mammalian estrogens (Clarkson T B, Anthony, M S, Morgan T M. Inhibition of postmenopausal atherosclerosis progression: a comparison of the effects of conjugated equine estrogens and soy phytoestrogens. J Clin Endocrinol Metab. 2001, 86:41-47), and are capable of interacting with the estrogen receptor on adipose tissue in many animal species including humans, rats, monkeys, and mice. (Naaz, A et al. 2003, supra; Linford N J, and Dorsa D M. 17 beta-Estradiol and the phytoestrogen genistein attenuate neuronal apoptosis induced by the endoplasmic reticulum calcium-ATPase inhibitor thapsigargin. Steroids. 2002, 67:1029-1040). Phytoestrogens are subdivided into three major classifications, coumestans, lignans, and isoflavones. Isoflavones have demonstrated significant positive effects with respect to reducing adipose deposition, reducing serum low density lipoproteins, inhibiting atherosclerosis, and the like, in subjects to which they were administered. (Bhathena, S J, et al. 2002; Naaz, A, et al. 2003; Wagner J D 2003; Kawakami Y et al. Regulative actions of dietary soy isoflavone on biological antioxidative system and lipid metabolism in rats. J. Agric. Food. Chem. 2004, 52:1764-1768; and Fang Y C et al. Effect of genistein supplementation on tissue genistein and lipid peroxidation of serum, liver and low-density lipoprotein in hamsters. 2004, 15:142-148).

Despite the positive effects observed with dietary supplementation in humans and rodents, there still exists a need to produce food or medicinal formulations for administration to companion animals, and even more so for administration to companion animals that have undergone a procedure to remove sex organs such as spaying or neutering. Ideally, such food or medicinal formulations, and the methods to use them, would facilitate the loss of body fat, minimize loss of lean body mass, and reduced oxidative stress damage in the animals.

SUMMARY OF THE INVENTION

In certain aspects, the present invention relates to compositions comprising one or more nutrients or bioactive substances that maximize body fat loss and minimize the loss of lean body mass in obese and overweight animals by simultaneously and/or synergistically inhibiting fat synthesis, promoting fat breakdown, and increasing fatty acid oxidation. Maximizing the loss of body fat and utilization of dietary calories as energy sources spare the lean body mass during weight loss in obese and overweight animals. In certain embodiments, the nutrients and bioactive substances are isoflavones, metabolites of isoflavones, conjugated linoleic acid, L-carnitine, or any other nutrient or bioactive substance that inhibits fat synthesis, promotes fat breakdown, or enhances fatty acid oxidation.

Thus, one aspect of the invention features a composition comprising one or more isoflavones or metabolites thereof, in an amount effective for weight management in an animal. In some embodiments, the composition further comprises conjugated linoleic acid or L-carnitine. The composition may be in the form of a foodstuff, dietary supplement, or pharmaceutical.

In certain embodiments, the composition comprises isoflavones including one or more of: daidzein, genistein, glycitein, biochanin A, formononetin, natural glycoside, isoflavone metabolite, chemically-synthesized isoflavone, or chemically-synthesized isoflavone analog. In specific embodiments, the isoflavones are soy isoflavones or metabolites thereof, such as equol.

Other aspects of the invention relate to methods and processes to prepare such compositions. Additional aspects of the present invention relate to methods useful for weight management in an animal utilizing compositions comprising isoflavones and/or the metabolites of isoflavones, and in some embodiments, conjugated linoleic acid or L-carnitine. The compositions and methods are effective for reducing body fat in an animal or for retaining lean body mass in an animal, by mechanisms including one or more of enhancing adipose tissue catabolism, enhancing fatty acid oxidation, or diminishing adipose tissue anabolism. The compositions and methods of the invention are particularly well suited for weight management in an animal that has been neutered, castrated, or spayed, or in an animal that is post-menopause or post-andropause.

Other features and advantages of the present invention will be understood by reference to the detailed description and the examples that follow.

DETAILED DESCRIPTION OF ILLUSTRATIVE EMBODIMENTS

Figure 1:
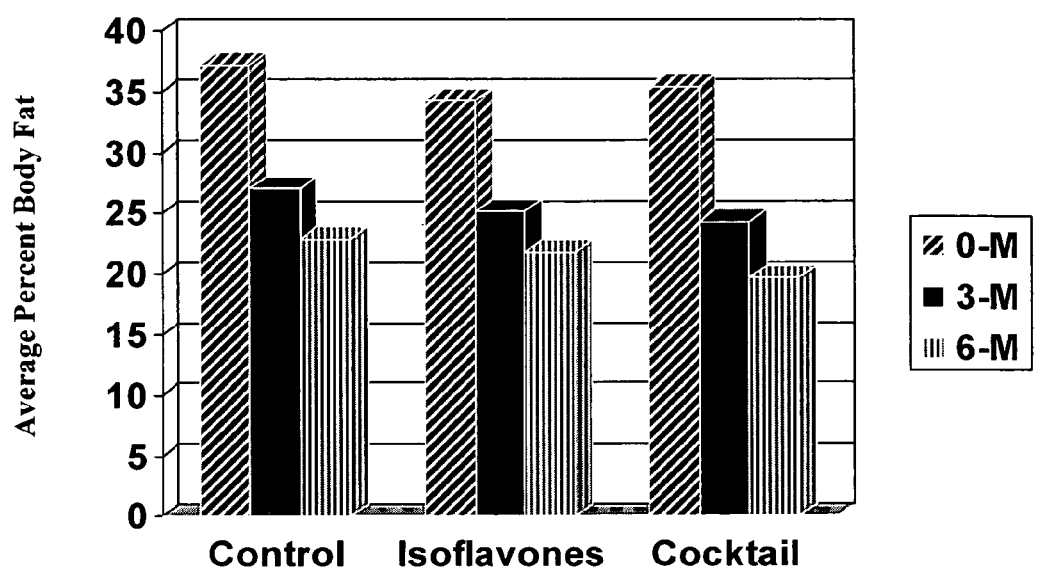
FIG. 1 shows changes in body fat content during a 6-month weight loss regimen in dogs.

As employed above and throughout the disclosure, the following terms, unless otherwise indicated, shall be understood to have the following meanings.

"Effective amount" refers to an amount of a compound, material, composition, and/or dosage form as described herein that may be effective to achieve a particular biological result. Such results may include, but are not limited to, reduction and/or prevention of obesity. Such effective activity may be achieved, for example, by causing the ingestion of compositions of the present invention.

"Mammal" refers to any of a class of warm-blooded higher vertebrates that nourish their young with milk secreted by mammary glands and have skin usually more or less covered with hair, and non-exclusively includes rodents (e.g., mice and rats), goats, cats, dogs, cows, pigs, sheep, horses, non-human primates, rabbits, ferrets, and guinea pigs, whether or not the animal is post-menopause, post-andropause, or has been castrated, spayed, or neutered.

"Obesity" refers to an increase in body weight beyond the limitation of skeletal and physical requirement, as the result of an excessive accumulation of fat in the body "Overweight" refers to weighing more than is normal or necessary, especially having more body weight than is considered normal or healthy for one's age or build. Overweight or obesity may sometimes be referred to herein as a numerical "score", using a body conditioning scoring system in which a BCS (body condition score) of 1-3 indicates too thin or underweight, BCS of 4-5 indicates ideal condition or weight, and BCS of 6-9 indicates overweight to obese.

A "weight control program" refers to a regimen designed to prevent and/or reduce obesity in an animal. Such a regimen may include, without limitation, the use of a particular diet, food, foodstuff, dietary supplement, or pharmaceutical; alone or in any suitable combination.

"Weight management" refers to the promotion of healthy weight loss and the promotion of healthy weight maintenance in an animal, whether or not the animal is on a formalized weight control program. The term encompasses the reduction of body fat and adipose tissue, the minimized loss of lean body mass, and the reduction of oxidative stress damage to tissues associated with obesity. The term also encompasses the prevention of weight gain, excessive weight gain, and obesity, and the enhancement of the formation of lean body mass. Weight management may be accomplished by, among other things, enhancing fat or adipose tissue catabolism, an enhancing fatty acid oxidation, and/or diminishing fat or adipose tissue anabolism.

In certain aspects, the present invention relates to compositions useful in the reduction and/or prevention of obesity in an animal, the compositions comprising one or more isoflavones, conjugated linoleic acid (CLA) and/or L-carnitine, and to methods of use thereof. Compositions and methods according to certain aspects of the invention are effective to enhance weight loss in overweight and obese animals. In other aspects of the invention, compositions and methods according to certain embodiments of the invention are effective for reducing fat accumulation in animals with normal body condition scores, thus preventing normal animals from becoming or remaining overweight or obese.

Without being limited to any theories or particular modes of action of the invention, certain embodiments of the invention are believed to be effective at specifically promoting loss of adipose tissue. Certain aspects of the invention are believed to be effective at optimizing fat loss in an animal by acting at three key steps: 1) increasing the catabolism of adipose tissue, 2) increasing fatty acid oxidation and 3) decreasing the anabolism of adipose tissue. Furthermore, according to certain aspects of the invention, optimizing fat loss during weight loss may prevent loss of lean body mass. In addition, isoflavones and metabolites of isoflavones, including equol and dihydrodaidzein, are believed to reduce tissue damage associated with obesity via their free radical scavenging activities.

As used herein, "adipose tissue" refers to the connective tissue comprising fat cells (also referred to as adipocytes) and their surrounding reticular fibers and reticular network. Adipose tissue is generally where the body deposits and stores excess fat. Adipose tissue encompasses, without limitation, white, brown, and yellow adipose tissue.

As used herein, "catabolism" refers to the metabolic breakdown of complex molecules into simpler molecules. With respect to the catabolism of adipose tissue, the term encompasses the metabolic breakdown of fat stores into energy and/or a reduction in the number or size of adipocytes.

As used herein, "anabolism" refers to the metabolic processes in which simple substances are synthesized into the complex materials. With respect to anabolism of adipose tissue, the term encompasses the formation of triglycerides, genesis of adipocytes, the generation of the adipose reticular network, and the like.

As used herein, "isoflavones" refers to 3-phenyl-chromones, isomeric forms of flavones in which the benzene group is attached to the 3 position of the benzopyran ring instead of the 2 position, and their respective metabolites. Whenever the term "isoflavones" is used herein, it is intended to encompass derivatives and metabolites of isoflavones, with particular examples of isoflavone derivatives as described herein. Isoflavones may be found in a number of sources, including, but not limited to, soy. Non-limiting examples of isoflavones include daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, formononetin, or any metabolites of isoflavones. Isoflavones and certain benefits to health derived from their use have been described in the scientific literature (see, e.g., Setchell K D R, Adlercreutz H. Mammalian lignans and phytoestrogens. Recent studies on their formation, metabolism and biological role in health and disease. In: Rowland I A, ed. The Role of Gut Microflora in Toxicity and Cancer. New York: Academic Press 1988: 315-345). For instance, soy has been found to reduce the risk of cardiovascular disease; reduce the risk of breast and prostate cancer; relieve hot flushes associated with menopausal estrogen deficiency; retard osteoporosis in postmenopausal women; reduce total amount of cholesterol, LDL cholesterol, and triglycerides in plasma; preserve cognitive functions in postmenopausal women; improve symptoms of hypertension and promote weight loss.

Isoflavones and metabolites are known to exhibit antioxidant activity. Equol (a metabolite of daidzein) has the greatest antioxidant activity of all the isoflavones tested (Setchell K R, Brown N M, Lydeking-Olsen E. The clinical importance of the metabolite equol-a clue to the effectiveness of soy and its isoflavones. J. Nutr. 2002, 132:3577-3584). In addition, another metabolite of daidzein, dihydrodaidzein, also appears to have free radical scavenging activities (Jiang F, Jones G T, Husband A J, Dusting G J. Cardiovascular protective effects of synthetic isoflavone derivatives in apolipoprotein E-deficient mice. J. Vas Res. 2003, 40: 276-284).

Isoflavones and metabolites are also known to exhibit estrogenic activity. Equol induces estrogen receptor (ER)-responsive transcription (estrogenic activity) more strongly than any other isoflavones. About 30-50% of the adult population do not biotransform daidzein into equol (J. Nutr. 132: 3577-3584, 2002). Daidzein and glycitein mimic estrogen in suppressing body fat accumulation in rats after surgically-induced menopause.

The isoflavone genistein has been shown to be an inhibitor of topoisomerase II (an enzyme involved in DNA duplication for cell proliferation). It also inhibits tyrosine protein kinase, thus providing anti-cancer properties. Genistein inhibits angiogenesis (also providing anti-cancer properties).

A possible mechanism by which isoflavones affect body composition has been suggested by a study showing that the isoflavones genistein and daidzein inhibited basal and insulin-stimulated lipogenesis and enhanced basal and epinephrine-stimulated lipolysis in rat adipocytes (Kandulska K, Nogowski L, Szkudelski T. Effect of some phytoestrogens on metabolism of rat adipocytes. Reprod Nutr Dev. 1999, 39:497-501).

As used herein, "carnitine" refers to a trimethylammonium (betaine) derivative of γ-amino-β-hydroxybutyric acid, formed from $N_8,N_8,N_8$-trimethyllysine and from γ-butyrobetaine. L-carnitine is an acyl carrier with respect to the mitochondrial membrane; it thus stimulates fatty acid oxidation. It is sometimes referred to as Vitamin Bt or Vitamin B7 (see, e.g., Fritz I B, Yue K T N, Long-chain carnitine acyltransferase and the role of acylcarnitine derivatives in the catalytic increase of fatty acid oxidation induced by carnitine, J. Lipid Res. 1963, 4: 279).

L-carnitine is a naturally occurring compound that plays an important role in energy production in an animal's body. L-carnitine transports activated fatty acids, e.g. acyl-CoA, into the mitochondrial matrix, which is the organelle responsible for energy production, for beta-oxidation. Beta oxidation is a process by which fatty acid is broken down for energy production. L-carnitine is synthesized from the amino acids lysine and methionine primarily in the liver and kidneys, and it is transported to other tissues. Higher concentrations of L-carnitine are found in tissues that use fatty acid as their primary energy source, such as skeletal and cardiac muscle, compared to other tissues. Meat, poultry, fish, and dairy products are rich dietary sources of L-carnitine.

As used herein, "conjugated linoleic acid (CLA)" is a collective term used to designate a mixture of positional and geometric isomers of the essential fatty acid linoleic acid (see, e.g., Chin S F, Liu W, Storkson J M, Ha Y L, M W Pariza, Dietary sources of conjugated dienoic isomers of linoleic acid, a newly recognized class of anticarcinogens, J. Food Comp. Anal. 1992, 5:185-197). CLA is found naturally in certain food sources, including red meat, cheese and whole milk.

CLA promotes fat breakdown in adipose tissue by enhancing hormone-sensitive lipase activity. CLA reduces the activity of lipoprotein lipase, a key enzyme for lipid synthesis in adipose tissue. Lipoprotein lipase is involved in releasing fatty acids from triacylglycerides. The released fatty acids are then taken up by adipocytes, re-esterified and stored as triacylglycerides in the adipocytes. In addition, CLA increases carnitine palmitoyltransferase (CPT) activity in both fat and skeletal muscle. CPT is the rate-limiting enzyme for fatty acid beta-oxidation.

The present invention relates to any animal, preferably a mammal; more preferably to cats, and most preferably to dogs.

According to an embodiment of the present invention, a composition is provided comprising one or more isoflavones, CLA and L-carnitine, the composition being effective for the reduction and/or prevention of obesity in animals. The inventors have demonstrated herein that a combination of isoflavones, CLA and L-carnitine is effective in promoting a reduction in body fat and in preserving lean body mass when administered to animals fed a low-calorie diet. In a certain preferred embodiments, the isoflavones are soy isoflavones.

According to another embodiment of the present invention, a composition is provided comprising one or more isoflavones, the composition being effective for the reduction and/or prevention of obesity in animals. In certain preferred embodiments, the isoflavones are soy isoflavones.

According to another embodiment of the invention, a composition is provided comprising one or more isoflavones, the composition being effective for preserving lean body mass in an animal. Preferably, the isoflavones are soy isoflavones. The inventors have demonstrated herein that compositions comprising isoflavones alone can reduce loss of lean body mass in animals on a weight control program.

Additional aspects of the invention relate to compositions and methods effective for reducing tissue damage associated with excess body fat. Non-limiting examples of tissue damage include the oxidative modification of DNA, RNA, proteins and lipids by oxidative stress. Oxidative stress consists of reactive oxygen species (ROS), such as hydroxyl radicals, and reactive nitrogen species (RNS), such as nitric oxide and its by-products including nitrate, nitrite, and peroxinitrite (Davi G, Falco A, Patrono C. Lipid peroxidation in diabetes mellitus. Antioxid Redox Signal. 2005, 7:256-268.; Kang D, Hamasaki N. Alterations of mitochondrial DNA in common diseases and disease states: aging, neurodegeneration, heart failure, diabetes, and cancer. Curr Med Chem. 2005; 12:429-441; Stocker R, Keaney J F Jr. Role of oxidative modifications in atherosclerosis. Physiol Rev. 2004, 84:1381-1478.). Increased oxidative stress has been linked with obesity. Isoprostanes has emerged as one of the most reliable approaches to assess oxidative stress status in vivo, serving as an important tool to explore the role of oxidative stress in the pathogenesis of chronic disease (Montuschi P, Barnes P J, Roberts L J 2nd. Isoprostanes: markers and mediators of oxidative stress. FASEB J. 2004 18:1791-1800.)

In one embodiment of the invention, a composition is provided comprising one or more isoflavones, the composition being effective for reducing tissue damage associated with obesity. Preferably, the isoflavones are soy isoflavones. In another embodiment of the invention, a composition is provided comprising one or more isoflavones, CLA and L-carnitine, the composition being effective for reducing tissue damage associated with obesity. Preferably, the isoflavones are soy isoflavones.

According to certain aspects of the invention, a composition of the invention may be useful as, for example, a diet, a food, a foodstuff, a dietary supplement, or a veterinary therapeutic product. The compositions may optionally contain a carrier, a diluent, or an excipient, chosen to be suitable for the intended use.

The compositions can be administered enterally, such as, for example, orally, intragastricly, or transpyloricly. Many factors that may modify the action of the composition can be taken into account by those skilled in the art; e.g., body weight, sex, diet, time of administration, route of administration, rate of excretion, condition of the subject, and reaction sensitivities and severities. Administration can be carried out continuously or periodically, such as once daily, or once with every meal.

As used herein, a "foodstuff" refers to any substance that can be used or prepared for use as food. As used herein, a "food" is a material consisting essentially of protein, carbohydrate and/or fat, which is used in the body of an organism to sustain growth, repair and vital processes and to furnish energy. Foods may also contain supplementary substances such as minerals, vitamins and condiments. Non-limiting examples of supplementary minerals include calcium, phosphorous, potassium, sodium, iron, chloride, boron, copper, zinc, manganese, iodine, selenium and the like. Non-limiting examples of supplementary vitamins include vitamin A, various B vitamins, vitamin C, vitamin D, vitamin E, and vitamin K. Additional dietary supplements may also be included, for example, niacin, pantothenic acid, inulin, folic acid, biotin and the like. As used herein, the term food includes beverages adapted for human or animal consumption.

As used herein, a "pharmaceutical" is a medicinal drug. A pharmaceutical may also be referred to as a medicament. As used herein, a "dietary supplement" is a product that is intended to supplement the diet; it may bear or contain any one or any combination of the following dietary ingredients: a vitamin, a mineral, an herb or other botanical, an amino acid, a dietary substance for use to supplement the diet by increasing the total daily intake (including, without limitation, enzymes or tissues from organs or glands), a concentrate, metabolite, constituent, or extract.

In certain embodiments of the invention, a diet or foodstuff is provided that is useful in the reduction and/or prevention of obesity in animals, the diet or foodstuff comprising one or more isoflavones, CLA, and/or L-carnitine.

Certain aspects of the invention are preferably used in combination with a complete and balanced food (for example, as described in National Research Council, 1985, Nutritional Requirements for Dogs, National Academy Press, Washington D.C., or Association of American Feed Control Officials, Official Publication 1996). That is, compositions comprising isoflavones, CLA and/or L-carnitine according to certain aspects of this invention are preferably used with a high-quality commercial food. As used herein, "high-quality commercial food" refers to a diet manufactured to produce the digestibility of the key nutrients of 80% or more, as set forth in, for example, the recommendations of the National Research Council above for dogs. Similar high nutrient standards would be used for other animals.

Certain aspects of the present invention relate preferentially to an animal diet or foodstuff which may be, for example, a wet, intermediate or dry composition (food), including pet treats. Wet food usually describes food which is sold in tins or foil bags, and has a moisture content of about 70 to about 90%. Dry food usually describes food which is of a similar composition, but with about 5 to about 15% moisture content and therefore is presented, for example, as small biscuit-like kibbles. Therefore, certain aspects of the present invention may to apply to canned, dry or intermediate moisture pet food products as those terms are recognized by those skilled in the art of pet food formulation and manufacturing.

The diet or foodstuff can be made according to any method known in the art such as, for example, that described in Waltham Book of Dog and Cat Nutrition, Ed. A T B Edney, Chapter by A. Rainbird, entitled "A Balanced Diet" in pages 57 to 74, Pergamon Press Oxford. Suitable starch sources include, without limitation, grains and legumes such as corn, rice, wheat, barley, oats, soy, and mixtures of these. Suitable protein sources may be selected from any suitable animal or vegetable protein source, including, but not limited to, meat.

Preferably, the concentrations of isoflavones, CLA and/or L-carnitine to be added to the diet or foodstuff are calculated on the basis of the energy content of the diet or foodstuff and of any additional nutrients which may be consumed by the animal. Preferably, a complete and balanced food comprises a diet or foodstuff according to certain embodiments of the invention.

According to certain aspects of the invention, the isoflavones, CLA and/or L-carnitine may be added at any time during the manufacture and/or processing of the diet or foodstuff, including, for example, at the end, as the last step before packaging.

According to certain aspects of the invention, preferred daily dose ranges for isoflavones may be from about 5 mg/day to about 5000 mg/day. Preferably the daily dose of isoflavones is from about 30 mg/day to about 500 mg/day, more preferably from about 80 mg/day to about 200 mg/day. Preferred daily dose ranges for L-carnitine may be from about 50 mg/day to about 5000 mg/day. Preferably, the daily dose of L-carnitine is from about 80 mg/day to about 500 mg/day, more preferably from about 100 mg/day to about 300 mg/day. Preferred daily dose ranges for CLA may be from about 50 mg/day to about 8000 mg/day. Preferably, the daily dose of CLA is from about 500 mg/day to about 6000 mg/day, more preferably from about 1000 mg/day to about 4000 mg/day.

The sources of each of the isoflavones, CLA and L-carnitine can be any suitable source, synthetic or natural. Preferred sources of isoflavones include, without limitation, any isoflavone-containing plants such as, for example, legumes, clovers, and kudzu root. Preferred legume sources of isoflavones include soy beans, chick peas, and other types of beans and peas which contain isoflavones. Preferred clover sources of isoflavones include red clover and subterranean clover. Preferred conjugated linoleic acid sources include hydrolyzed sunflower oil, or synthetic isomers of CLA or synthetic CLA analogs or a combination of two or more thereof. More preferably, the source of CLA is hydrolyzed sunflower oil. Preferred sources of L-carnitine include, without limitation, L-carnitine and any L-carnitine derivatives such as, for example, L-carnitine fumarate, and L-carnitine tartrate.

Since isoflavones, conjugated linoleic acid and L-carnitine are present in food, it may be preferable to determine the concentration of each which is present in the ingredients of the diet/foodstuff and then add sufficient quantities to bring the total concentration of each up to the required levels, according to certain embodiments of the invention.

According to certain aspects of the invention, isoflavones, CLA and/or L-carnitine may be provided in a diet which can comprise any suitable pet food formulation which also provides adequate nutrition for the animal. For example, a typical canine diet for use in the present invention may contain about 18-50 wt % crude protein, about 4-30 wt % fat, about 5-50% carbohydrate, and about 2-20 wt % total dietary fiber. However, no specific percentages or ratios are required. Preferably, the animal is fed a low-calorie diet supplemented with isoflavones, CLA and L-carnitine to reduce and/or prevent obesity. A traditional low caloric diet for canines comprises about 1400 Kcal per pound of food, about 25% protein, about 6% fat, and about 7% crude fiber.

According to another aspect of the invention, there is provided a dietary supplement useful for the reduction and/or prevention of obesity in an animal, the supplement comprising one or more isoflavones, CLA and/or L-carnitine. Preferably, the dietary supplement comprises a combination of isoflavones, CLA and L-carnitine. In a preferred embodiment, the isoflavones comprise soy isoflavones. The dietary supplement can be in any convenient form, including, without limitation, liquid, solid, or powder form. Solid forms of the supplement include, but are not limited to, a pill, biscuit, or treat.

According to certain embodiments of the invention, a dietary supplement can be formed as a foodstuff with higher levels of isoflavones, CLA and/or L-carnitine which requires "dilution" before feeding to an animal. The supplement may be in any form, including, without limitation, solid (e.g. a powder), semi-solid (e.g. a food-like consistency/gel) or a liquid. The supplement may be administered to the animal in any suitable manner. For example, the liquid form can conveniently be mixed in with food or fed directly to the animal, such as, for example, via a spoon or via a pipe-like device. In certain embodiments, the supplement can be high in all three components of isoflavones, CLA and L-carnitine or can be a combined pack of two or more components, having the required concentrations of isoflavones, CLA and/or L-carnitine separately or in any suitable combination.

Another embodiment of the present invention relates to a process for the preparation of a composition useful in the reduction and/or prevention of obesity in an animal, the composition comprising one or more isoflavones, CLA, and/or L-carnitine. Preferably, the process comprises the steps of mixing together suitable ingredients to yield a mixture, optionally heating the mixture to cook any raw food ingredients; and forming the mixture into a form suitable for consumption.

Another embodiment of the invention relates to a method for the reduction and/or prevention of obesity in an animal by administering to the animal an effective amount of a composition comprising one or more isoflavones, CLA and/or L-carnitine. Preferably, the method comprises the administration of an effective amount of a combination of isoflavones, CLA and L-carnitine. Preferably, the isoflavones comprise soy isoflavones. Preferably, the isoflavones, CLA and/or L-carnitine may be administered to an animal in a diet, food, foodstuff, dietary supplement, or pharmaceutical composition as, for example, described herein.

Another embodiment of the invention relates to a method for the preservation of lean body mass in an animal by administering to the animal of an effective amount of a composition comprising one or more isoflavones. In a preferred embodiment, soy isoflavones are administered. Preferably, the isoflavones may be administered to an animal in a suitable diet, food, foodstuff, dietary supplement, or pharmaceutical composition as, for example, described herein.

Another embodiment of the invention relates to compositions for weight management in an animal that has a permanently reduced level of sex hormones circulating in the plasma. Sex hormones are typically at a permanently reduced level subsequent to neutering, castration, spaying, ovariectomy, or ovariohysterectomy, and the like, or at reduced levels due to a congenital condition, or at reduced levels because the animal is post-menopause or post-andropause. The sex hormones may be androgens, estrogens, or both. In a preferred embodiment, the composition comprises one or more isoflavones and their metabolites, and optionally, CLA and L-carnitine, with the isoflavones preferably being soy isoflavones and their metabolites. In a more preferred embodiment, the composition comprises one or more isoflavones, and preferably, the isoflavones are soy isoflavones.

As used herein, "neutered," refers to the animal lacking or having imperfectly developed or nonfunctional generative organs, whether such condition occurs congenitally, by natural development processes, or through intervening surgery.

As used herein, "castrate" refers to the removal of the testicles of a male animal.

As used herein, "spay" refers to the removal of the ovaries of a female animal.

Still another embodiment of the invention relates to a method for weight management in an animal that has a permanently reduced level of sex hormones circulating in the plasma. Sex hormones are typically at a permanently reduced level subsequent to neutering, castration, spaying, ovariectomy, or ovariohysterectomy, and the like, or at reduced levels due to a congenital condition, or at reduced levels because the animal is post-menopause and post-andropause. The sex hormones may be androgens, estrogens, or both. In a preferred embodiment, the method comprises causing the regular ingestion by the animal of an effective amount of a composition comprising one or more isoflavones, CLA and L-carnitine, with the isoflavones preferably being soy isoflavones. In a more preferred embodiment, the method comprises the regular ingestion by the animal of an effective amount of a composition comprising one or more isoflavones, and preferably, the isoflavones are soy isoflavones. The composition ingested by the animal may be administered in the solid or liquid form of a foodstuff, a dietary supplement, a pharmaceutical, or a pet treat.

The invention is further demonstrated in the following examples. All of the examples are actual examples. The examples are for purposes of illustration and are not intended to limit the scope of the present invention.

EXAMPLE 1

Weight Loss

Overweight dogs (Male: >22% Body Fat; Female >26% Body Fat) were used. Group 1 (Control diet) consisted of 9 Labrador Retrievers (LRs) and 6 Siberian Huskies (SHs). Group 2 (Isoflavone diet) consisted of 8 LRs and 6 SHs. Group 3 (Cocktail diet) consisted of 7 LRs and 8 SHs.

Animals fed the Control diet (Group 1) received a traditional low caloric diet: 1400 Kcal/lb, 25% protein, 6% fat, 7% crude fiber. Animals fed the Isoflavone diet (Group 2) were fed the control diet containing 10% Soy Germ Meal (SGM). Animals fed the Cocktail diet (Group 3) were fed the control diet containing 10% SGM, 1.5% conjugated linoleic acid (CLA), and 100 parts per million (ppm) l-carnitine.

All dogs were given a pre-study MER determination. All dogs were fed 70% of their maintenance energy requirement (MER) during the first 3 months of weight loss. At 3 months, animals were assayed by Dual Energy X-ray Absorptiometry (DEXA). Dogs that failed to reach the ideal body fat level (male: <17%; female: <20%) after the first 3 months of weight loss were fed 55% of their MER to induce further weight loss. The body fat levels of these dogs were again assessed by DEXA at 6 months.

The following measurements were made for each animal:
Body weight, body condition score, DEXA.
Plasma concentrations of isoflavones and their metabolites
Blood leptin
Intravenous glucose tolerance test
Oxidative stress measurement (isoprostanes: 8-iso-prostaglandin F2α, formed from arachidonic acid in phospholipids by free radical reaction): 3-month samples Results are shown in FIGS. 1-7. After 6-months of weight loss, The percentages of dogs that had their body fat levels reduced to the ideal levels were 53.3%, 64.3%, and 66.6% for the control, isoflavone, and cocktail diets, respectively. The percentages of Labrador Retrievers that had their body fat levels reduced to the ideal levels were 66.7%, 75%, and 85.7% for the control, isoflavone, and cocktail diets, respectively. The percentages of Siberian Huskies that had their body fat levels reduced to the ideal levels were 33.3%, 50%, and 50% for the control ,isoflavone, and cocktail diets, respectively.

Figure 2:
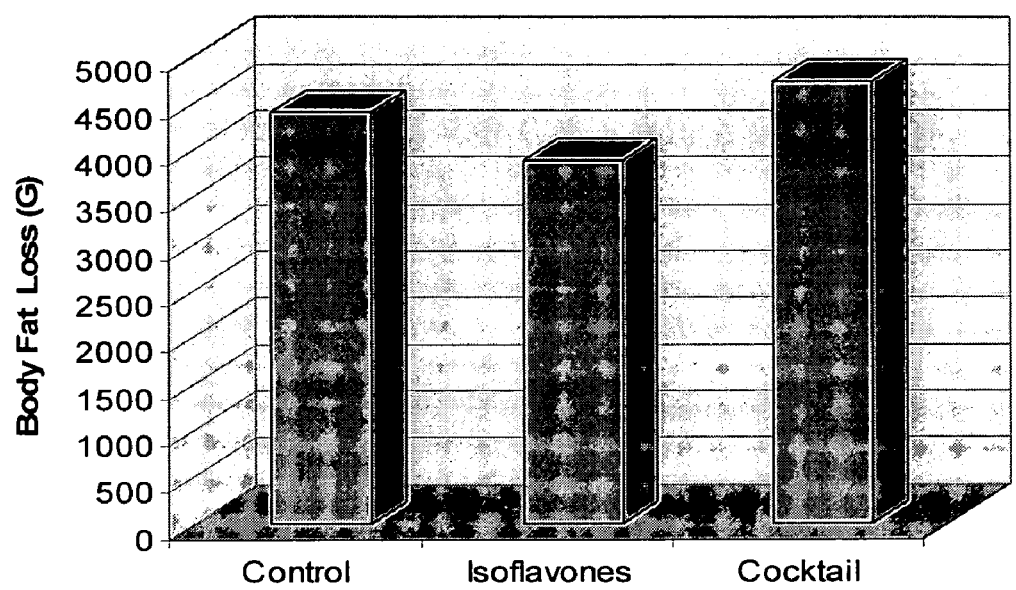
FIG. 2 shows 3-month DEXA results for loss of body fat. P=0.018 for isoflavone vs. cocktail diets.

Body fat loss was not different between control diet and isoflavone diet, but was observed to increase in the cocktail diet as compared with the control diet. Body fat loss was significantly different between isoflavone diet and cocktail diet (FIG. 1, FIG. 2).

Figure 3:
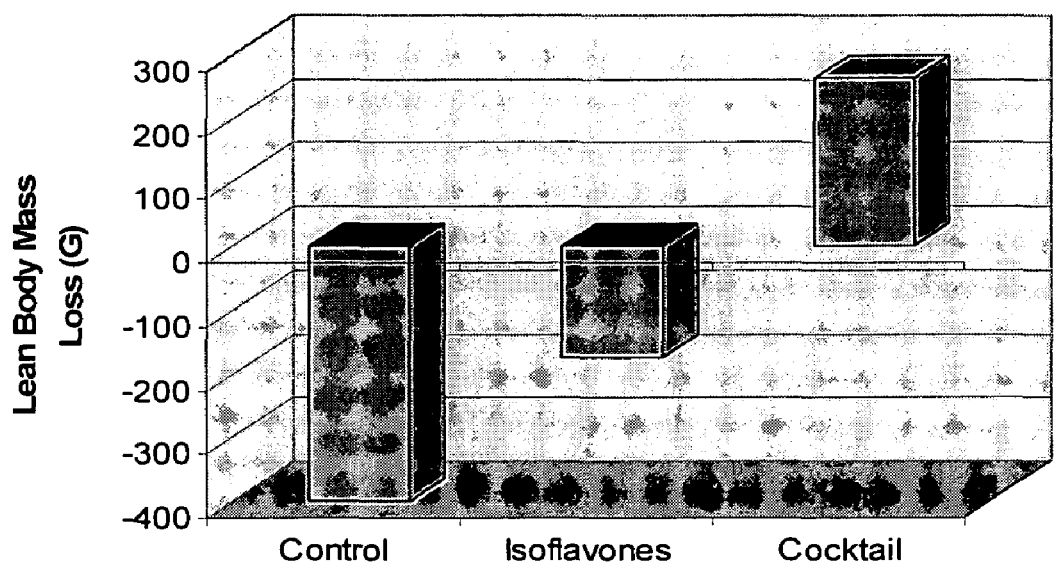
FIG. 3 shows 3-month DEXA results measuring the change in lean body mass. Control vs. cocktail, p=0.006

Dogs fed the control diet lost lean body mass regardless of breed. Dogs on the cocktail diet increased lean body mass (p=0.007, 265 g vs. −399.5 g in control dogs). Lean body mass loss was also reduced in dogs fed the isoflavone diet (FIG. 3).

Figure 4:
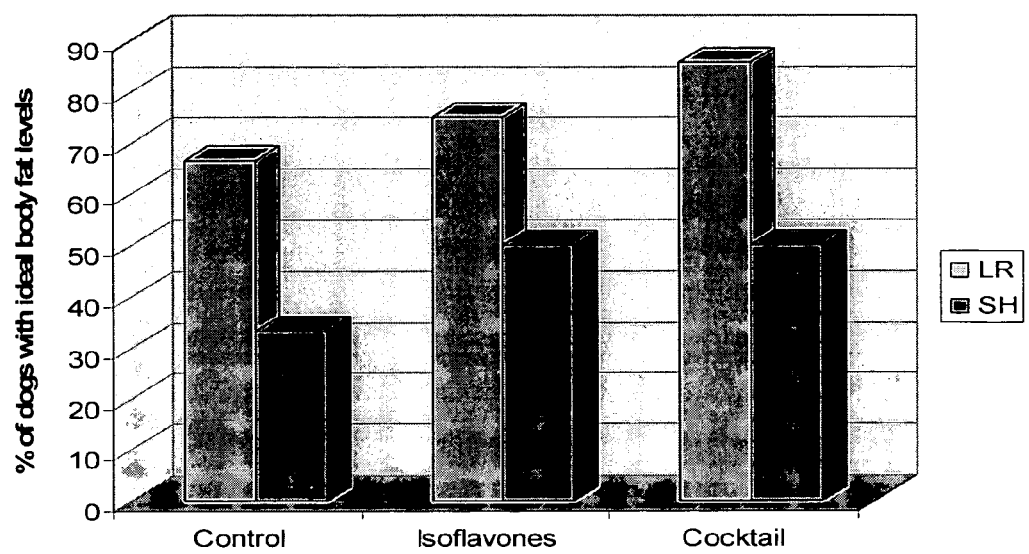
FIG. 4 shows the percentage of dogs whose body fat levels reduced to the ideal levels after 6 months of weight loss. In both breeds, higher percentages of dogs in isoflavones and cocktail groups had their body fat levels reduced to ideal levels (male: ≦17%; female: ≦20%) compared with control dogs.

In both breeds, higher percentages of dogs in isoflavone and cocktail groups had their body fat levels reduced to ideal levels (male: ≦17%; female: ≦20%) compared with control dogs (FIG. 4).

Figure 5:
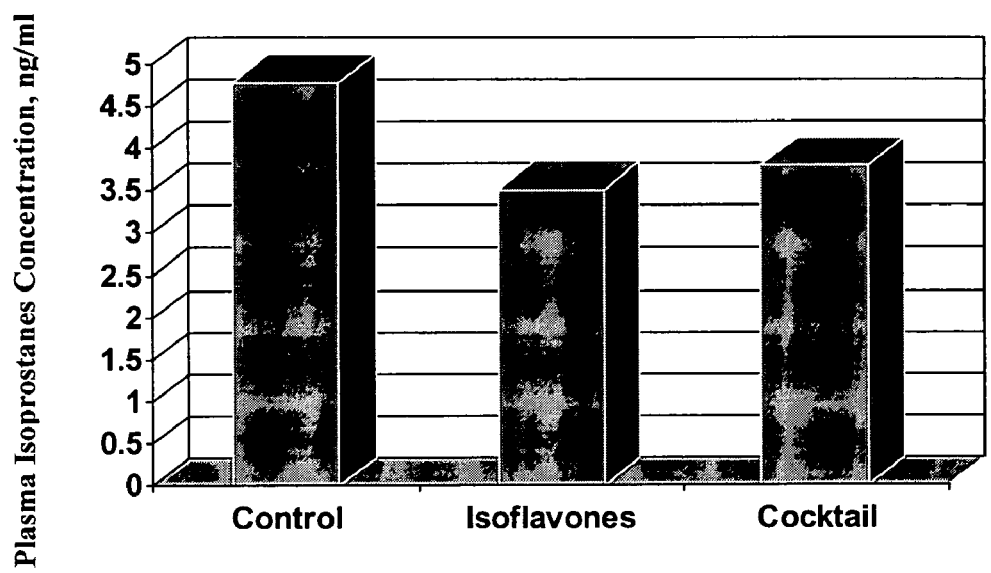
FIG. 5 shows 3-month results for the oxidative stress (damage) marker plasma isoprostanes concentration (in ng/ml). P=0.009 for control vs. isoflavones. P=0.037 for control vs. cocktail.

Both isoflavone and cocktail diets significantly reduced plasma isoprostanes (a lipid oxidative damage marker), compared with control diet (FIG. 5).

Figure 6:
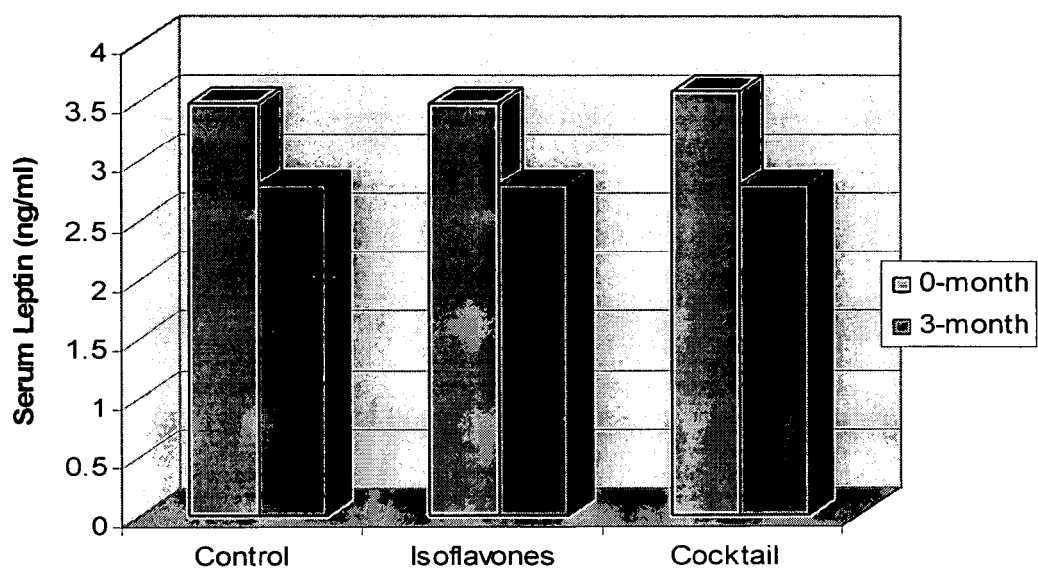
FIG. 6 shows baseline and 3-month results for serum leptin concentrations. In all three groups, serum leptin concentrations were significantly reduced after 3 months of weight loss compared with baseline.
Figure 7:
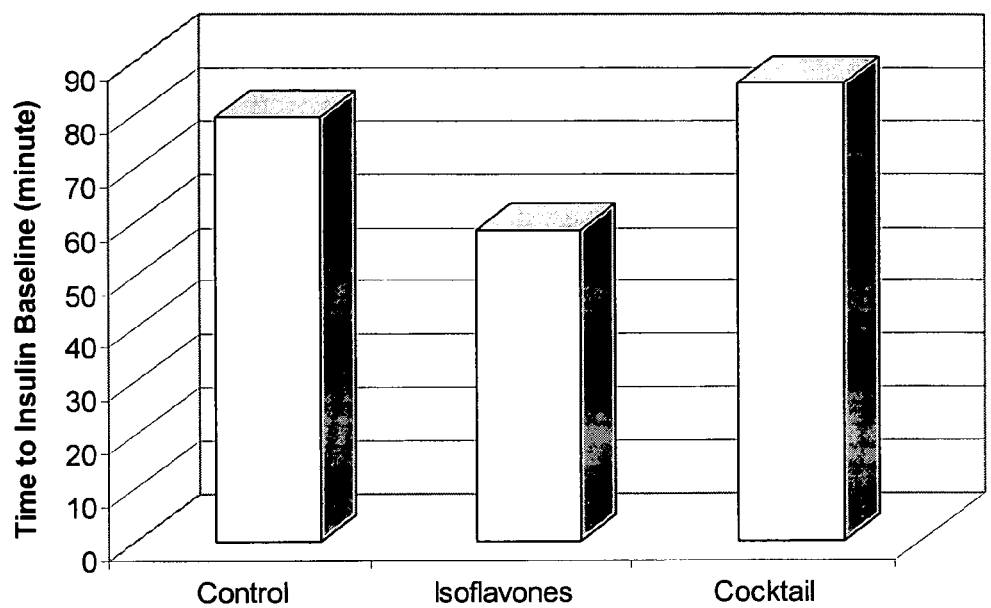
FIG. 7 shows isoflavones significantly improved time to insulin baseline in overweight dogs after 6-month of weight loss.

In all three groups (control, isoflavone and cocktail diets), serum leptin concentrations were significantly reduced after 3 months of weight loss compared with baseline (FIG. 6). Isoflavone-fed dogs showed significantly improved time to insulin baseline after 6-month of weight loss (FIG. 7).

Figure 8A:
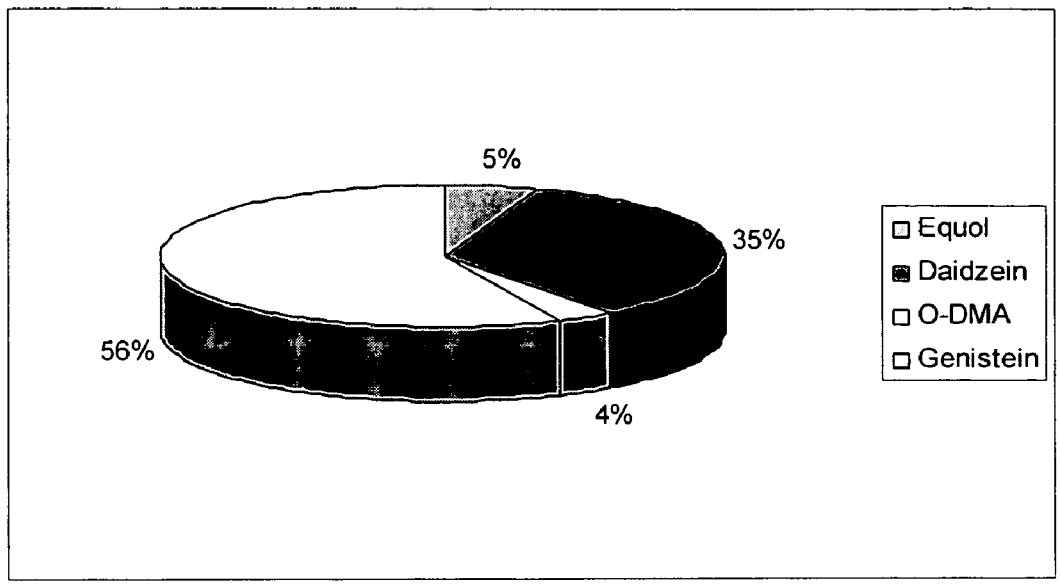
FIG. 8 is a chart showing the difference in metabolic profiles of isoflavones and their metabolites in the blood of dogs and humans.
Figure 8B:
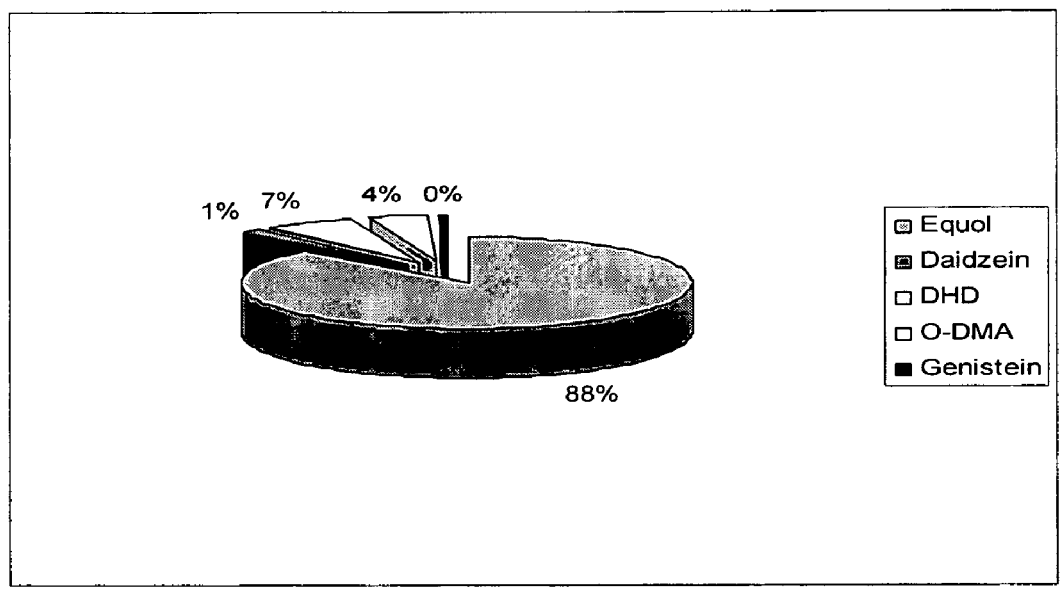

The metabolic profiles of isoflavones and their metabolites in the blood of humans (FIG. 8A) and dogs (FIG. 8B) were compared. Equol was determined to be the predominant form of isoflavone metabolite in the blood of the dogs tested (FIG. 8B).

EXAMPLE 2

Weight Management

Non-obese dogs that were spayed or neutered (Male: <17.5% Body Fat; Female <20% Body Fat, referred to as "normal" dogs) were used in the study. Group 1 (Control diet) consisted of 13 Labrador Retrievers (LRs). Group 2 (Isoflavone diet) consisted of 14 LRs. Group 3 (Cocktail diet) consisted of 15 LRs.

Animals fed the Control diet (Group 1) received a standard superpremium diet: 1900 Kcal/lb, 30% protein, 17% fat. Animals fed the Isoflavone diet (Group 2) were fed the control diet containing 10% Soy Germ Meal (SGM). Animals fed the Cocktail diet (Group 3) were fed the control diet containing 10% SGM, 1.5% conjugated linoleic acid (CLA), and 100 parts per million (ppm) l-carnitine.

The maintenance energy requirement (MER) of all dogs was determined prior to the feeding study. All dogs were fed 125% of their MER during the 12 months of feeding study.

Figure 9:
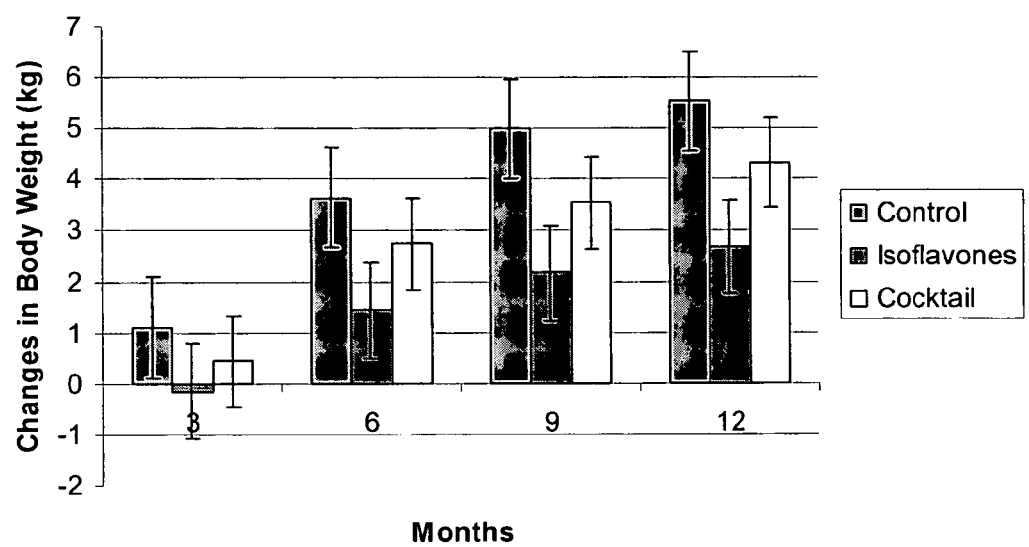
FIG. 9 shows that weight gain in normal dogs was significantly (p<0.05) lower in the isoflavones group than in the control group after 9 and 12 months of feeding. Throughout the 12-month study, the average weight gain in the control dogs was twice as much as that of the isoflavone-fed dogs.

The following measurements were made for each animal:
Body weight, body condition score, DEXA.
Plasma concentrations of isoflavones and their metabolites Weight Management Results Weight gain in normal dogs was significantly lower in the isoflavones group than in the control group after 9 (P=0.043, Control vs. Isoflavone group ), and 12 months (P=0.041, Control vs. Isoflavone group ) of feeding. Throughout the 12-month study, the average weight gain in the control dogs was twice as much as that of the isoflavone-fed dogs (FIG. 9).

Figure 10:
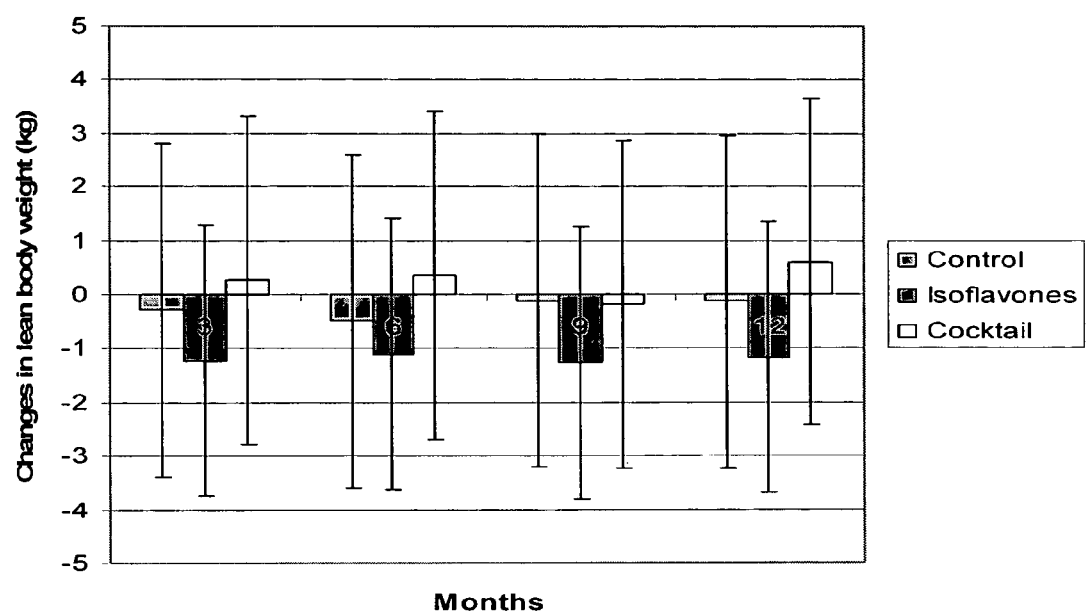
FIG. 10 shows that there was no difference in lean body mass changes among the three groups of dogs over the 12-month feeding study, indicating that the significantly higher weight gain in the control dogs was due to higher body fat accumulation in normal dogs.

There was no difference in lean body mass changes among the three groups of dogs over the 12-month of feeding study, indicating that the significantly higher weight gain in the control dogs was due to higher body fat accumulation in normal dogs (FIG. 10).

Figure 11:
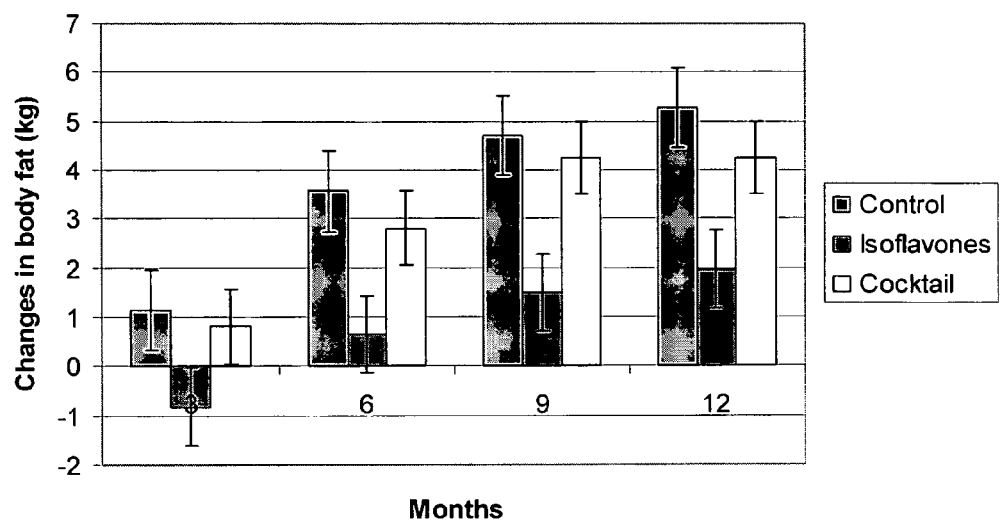
FIG. 11 shows that both control and cocktail groups gained significantly more body fat than the isoflavone group. Control dogs had 5, 3, and 2.7 times more average body fat gain than the isoflavone-fed dogs after 6, 9, and 12 months of feeding, respectively. The cocktail-fed dogs had 4.4, 2.8, and 2.2 times more average body fat gain than the isoflavone-fed dogs after 6, 9, and 12 months of feeding, respectively.

Both control and cocktail groups gained significantly more body fat than the isoflavone group. Control dogs had 5, 3, and 2.7 times more average body fat gain than the isoflavone-fed dogs after 6 (P=0.013, Control vs. Isoflavone group), 9 (P=0.007, Control vs. Isoflavone group ) and 12 months (P=0.006, Control vs. Isoflavone group ) of feeding, respectively. The cocktail-fed dogs had 4.4, 2.8, and 2.2 times more average body fat gain than the isoflavone-fed dogs after 6 (P=0.05, Cocktail vs. Isoflavone group ), 9 (P=0.014, Cocktail vs. Isoflavone group )and 12 (P=0.041, Cocktail vs. Isoflavone group ) months of feeding, respectively (FIG. 11).

Figure 12:
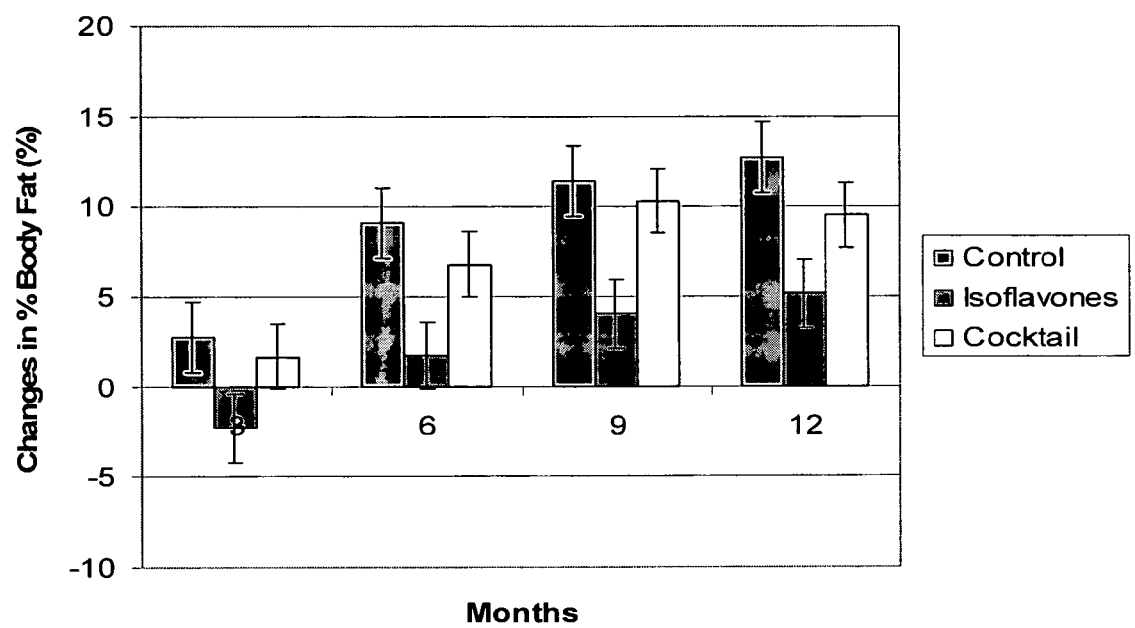
FIG. 12 shows that control group had 5, 2.8, and 2.5 fold increase in the percentage of the body fat than the isoflavone-fed dogs after 6, 9, and 12 months of feeding, respectively. The cocktail-fed dogs had 3.9, 2.6, and 1.9 times more average body fat gain than the isoflavone-fed dogs after 6, 9, and 12 months of feeding, respectively.

The control group had 5, 2.8, and 2.5 fold increase in the percentage of the body fat than the isoflavone-fed dogs after 6 (P=0.011, Control vs. Isoflavone group ), 9 (P=0.009, Control vs. Isoflavone group) and 12 months (P=0.008, Control vs. Isoflavone group) of feeding, respectively. The cocktail-fed dogs had 3.9, 2.6, and 1.9 times more average body fat gain than the isoflavone-fed dogs after 6 (P=0.06, Cocktail vs. Isoflavone group ), 9 (P=0.02, Cocktail vs. Isoflavone group ) and 12 months (P=0.098, Cocktail vs. Isoflavone group) of feeding, respectively (FIG. 12).

The disclosures of each patent, patent application and publication cited or described in this document are hereby incorporated herein by reference, in their entirety.

Various modifications of the invention, in addition to those described herein, will be apparent to those skilled in the art from the foregoing description. Such modifications are also intended to fall within the scope of the appended claims.

What is claimed is:

1. A method for reducing body fat while maintaining or increasing lean body mass and reducing obesity-related oxidative stress in an overweight animal on a calorie restricted diet, comprising the steps of:
    a) identifying an overweight animal;
    b) placing the animal on a calorie restricted diet; and
    c) causing the animal to regularly ingest a combination of L-carnitine, conjugated linoleic acid (CLA), and at least one isoflavone or metabolite thereof, such that the animal receives on a daily basis about 5-5,000 mg isoflavone, about 50-5,000 mg L-carnitine, and about 50-8,000 mg CLA, wherein the regular ingestion of the combination results in an increase in reduction in body fat and maintenance or increase in lean body mass in the animal, as compared with an equivalent animal on an equivalent diet that does not regularly ingest the combination.

2. The method of claim 1, wherein the combination is included in a foodstuff, dietary supplement, or pharmaceutical.

3. The method of claim 2, wherein the foodstuff comprises a pet food or pet treat.

4. The method of claim 2, wherein the dietary supplement is a liquid.

5. The method of claim 2, wherein the dietary supplement is a solid.

6. The method of claim 1, wherein the isoflavones include one or more of daidzein, genistein, glycitein, biochanin A, formononetin, a natural glycoside, an isoflavone metabolite, or a chemically-synthesized isoflavone.

7. The method of claim 1, wherein the isoflavones include one or more soy isoflavones or metabolites thereof.

8. The method of claim 7, wherein the soy isoflavone metabolites include equol.

9. The method of claim 1, wherein the animal is a human.

10. The method of claim 1, wherein the animal is a dog.

11. The method of claim 1, wherein the animal is a cat.

12. The method of claim 1, wherein the animal has been neutered, castrated, or spayed.

13. The method of claim 1, wherein the animal is postmenopausal or postandropausal.

14. The method of claim 1 wherein the animal receives about 80-200 mg of isoflavones, about 100-300 mg of L-carnitine, and about 1,000-4,000 mg of CLA daily.

\* \* \* \* \*